US00PP33735P3

(12) United States Plant Patent
Adams

(10) Patent No.: US PP33,735 P3
(45) Date of Patent: Dec. 14, 2021

(54) RASPBERRY PLANT NAMED 'ENDURANCE'

(50) Latin Name: *Rubus idaeus*
Varietal Denomination: ENDURANCE

(71) Applicant: PLANT SCIENCES, INC., Watsonville, CA (US)

(72) Inventor: Scott W. Adams, Watsonville, CA (US)

(73) Assignee: PLANT SCIENCES, INC., Watsonville, CA (US)

( * ) Notice: Subject to any disclaimer, the term of this patent is extended or adjusted under 35 U.S.C. 154(b) by 4 days.

(21) Appl. No.: 17/093,282

(22) Filed: Nov. 9, 2020

(65) Prior Publication Data

US 2021/0144896 P1 May 13, 2021

Related U.S. Application Data

(60) Provisional application No. 62/934,263, filed on Nov. 12, 2019.

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ... A01H 5/08; A01H 5/02; A01H 5/00; A01H 6/74; A01H 6/749; A01H 6/7499
See application file for complete search history.

(56) References Cited

U.S. PATENT DOCUMENTS

PP31,716 P3 * 5/2020 Adams ..... A01H 5/08 Plt./204

* cited by examiner

*Primary Examiner* — June Hwu
(74) *Attorney, Agent, or Firm* — Foley & Lardner LLP

(57) ABSTRACT

This invention relates to a new and distinct everbearing variety of raspberry plant named 'ENDURANCE'. The new variety is primarily adapted to the growing conditions of the central coast of California and is characterized by the following: late-season primocane production with medium to large sized fruit of medium-red coloration. Fruit is of consistent conic shape, releases easily from receptacle, possesses medium gloss and fair flavor. Foliage is flat to slightly convex, medium green; possessing weak rugosity, weak gloss and equal 3-5 foliates. Primocanes have an absent or very weak waxy coat, medium thorn density of small dark purple spines and have very weak anthocyanin coloration.

5 Drawing Sheets

Latin name of the genus and species of the plant claimed: *Rubus idaeus*.

Variety denomination: 'ENDURANCE'.

BACKGROUND

The present invention relates to a new and distinct everbearing raspberry variety designated 'ENDURANCE'. This new variety is a result of a controlled cross made in 2008 in Watsonville, Calif. between raspberry variety 'GRANDEUR' (patented, U.S. Plant Pat. No. 20,459) as the female parent and raspberry variety '04.3891' (unpatented) as the male parent in an ongoing breeding program. The variety is botanically known as *Rubus idaeus* and was tested as 'PS-08.056-18' and 'PS-5618'.

The seedling resulting from the aforementioned cross was asexually propagated by dormant canes in Santa Cruz County, Calif. and was subsequently selected by the inventor from a controlled breeding plot in Watsonville, Calif. in 2010. After its selection, the new variety was further asexually propagated by dormant canes, roots and non-dormant root shoot cuttings in Santa Cruz County, Calif., San Joaquin County, Calif. and Siskiyou County, Calif. The new variety was then extensively tested over the next several years in fruiting fields in Santa Cruz County, Calif. and has performed successfully in grower fields in USDA zones 9-10.

This propagation has demonstrated that the combination of traits disclosed herein as characterizing the new variety are fixed and remain true to type through successive generations of asexual reproduction.

SUMMARY

'ENDURANCE' is primarily adapted to the climate and growing conditions of the central coast of California. This region provides the necessary year-round temperatures required for it to produce and maintain a strong vigorous plant and to remain in fruit production from July through December on primocanes and in the ensuing year from May through July on the floricanes. The following traits have been repeatedly observed and are determined to be unique characteristics of 'ENDURANCE', which in combination distinguish this raspberry plant as a new and distinct variety:

1. Dark purple spines
2. Late fruit yield
3. Medium red fruit color
4. Absent to very weak primocane glaucosity
5. Fair flavor The raspberry variety that is believed to be most closely related to the new raspberry variety 'ENDURANCE' is the raspberry variety 'GRANDEUR' (patented, U.S. Plant Pat. No. 20,459). In comparison to the similar raspberry variety 'GRANDEUR', 'ENDURANCE' differs by the following combination of characteristics described in Table 1:

COMPARISON BETWEEN ENDURANCE AND GRANDEUR

TABLE 1

| Characteristic | 'ENDURANCE' | 'GRANDEUR' (US PP20,459) |
|---|---|---|
| Primocane waxy coat (glaucosity) | Absent to very weak | Absent to very weak |
| Predominate number of leaflets | Equal 3-5 | Always 3 |
| Leaf shape (cross section) | Flat to slightly convex | Flat to slightly convex |
| Rugosity | Weak | Strong |
| Color mature fruit | RHS 43A Medium red | RHS 42A Medium red |
| Thorn Tip Coloration | N186B Greyed-purple | 180C Greyed-red |
| Relative number of pedicel thorns | 26.9 Many | 16.2 Medium |

'ENDURANCE' differs from its sibling raspberry variety 'MAJESTIC' (patented, U.S. Plant Pat. No. 31,716) by the following combination of characteristics described in Table 2:

COMPARISON BETWEEN ENDURANCE AND MAJESTIC

TABLE 2

| Characteristic | 'ENDURANCE' | 'MAJESTIC' (U.S. Plant Pat. No. 31,716) |
|---|---|---|
| Time of fruiting (primocane) | Late | Medium |
| Terminal leaf shape | Lobed | Cordate |
| Leaf shape (cross section) | Flat to slightly convex | Slightly convex |
| Rugosity | Weak | Medium |
| Relative size of drupes | Large | Medium |
| Glossiness (fruit) | Medium | High |
| Adherence of receptacle | Very weak | Weak |
| Flavor | Fair | Very good |

'ENDURANCE' differs from its parents, 'GRANDEUR' and '04.3891', by the following combination of characteristics described in Table 3:

COMPARISON BETWEEN ENDURANCE, GRANDEUR AND 04.3891

TABLE 3

| Characteristic | 'ENDURANCE' | 'GRANDEUR' (U.S. Plant Pat. No. 20,459) | '04.3891' |
|---|---|---|---|
| Productivity | High | High | Medium |
| Glossiness (fruit) | Medium | Medium | High |
| Firmness (fruit) | Medium to high | Very high | Medium to low |
| Adherence of receptacle | Very weak | Very weak | Medium |
| Primocane time of fruiting | Late | Medium | Medium |
| Fruit size | Medium to large | Medium | Large |
| Flavor | Fair | Good | Good |

For identification, a series of molecular markers have been determined for this new variety.

BRIEF DESCRIPTION OF THE DRAWINGS

The accompanying color photographs illustrate the overall appearance of typical specimens of the new raspberry variety 'ENDURANCE' at various stages of development as true as reasonably possible with color reproductions of this type. Color in the photographs may differ slightly from the color value cited in the detailed botanical description which accurately describes the color of 'ENDURANCE'. The depicted plant and plant parts of the new raspberry variety 'ENDURANCE' were taken in Watsonville, Calif. and are approximately 2 to 16 months old.

DETAILED BOTANICAL DESCRIPTION

Figure 1:
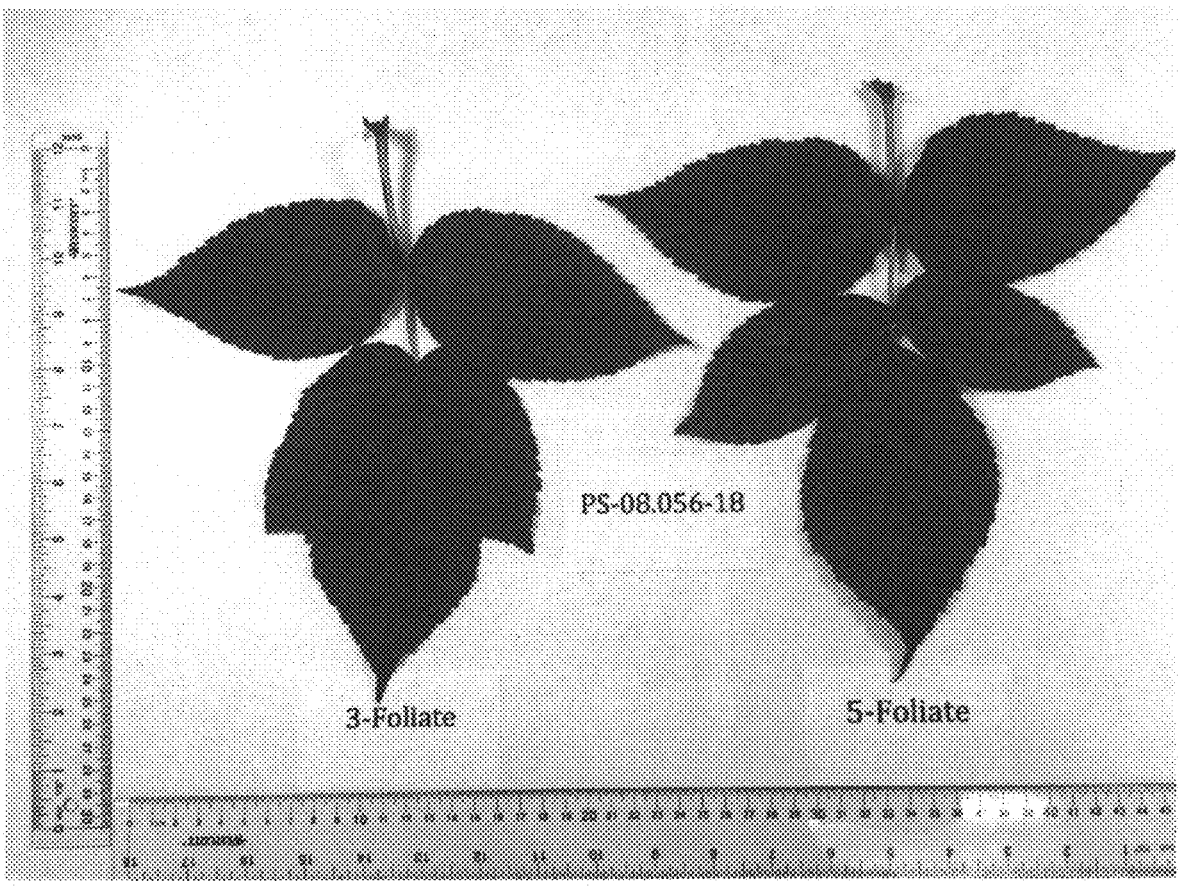
FIG. 1 shows typical leaf shape, foliate and rugosity characteristics of 'ENDURANCE' taken in the month of September 2020.
Figure 2:
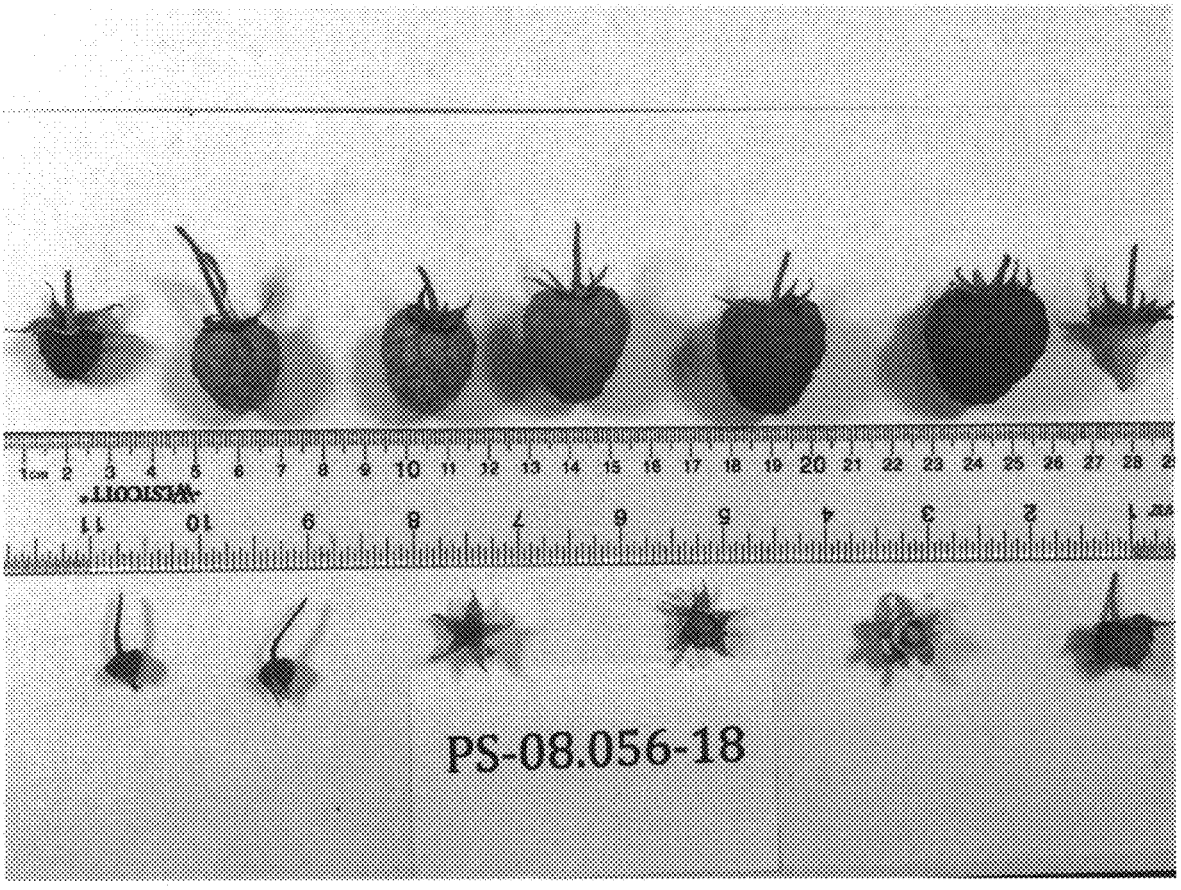
FIG. 2 shows bud, flower and fruit characteristics of 'ENDURANCE' taken in the month of September 2020.
Figure 3:
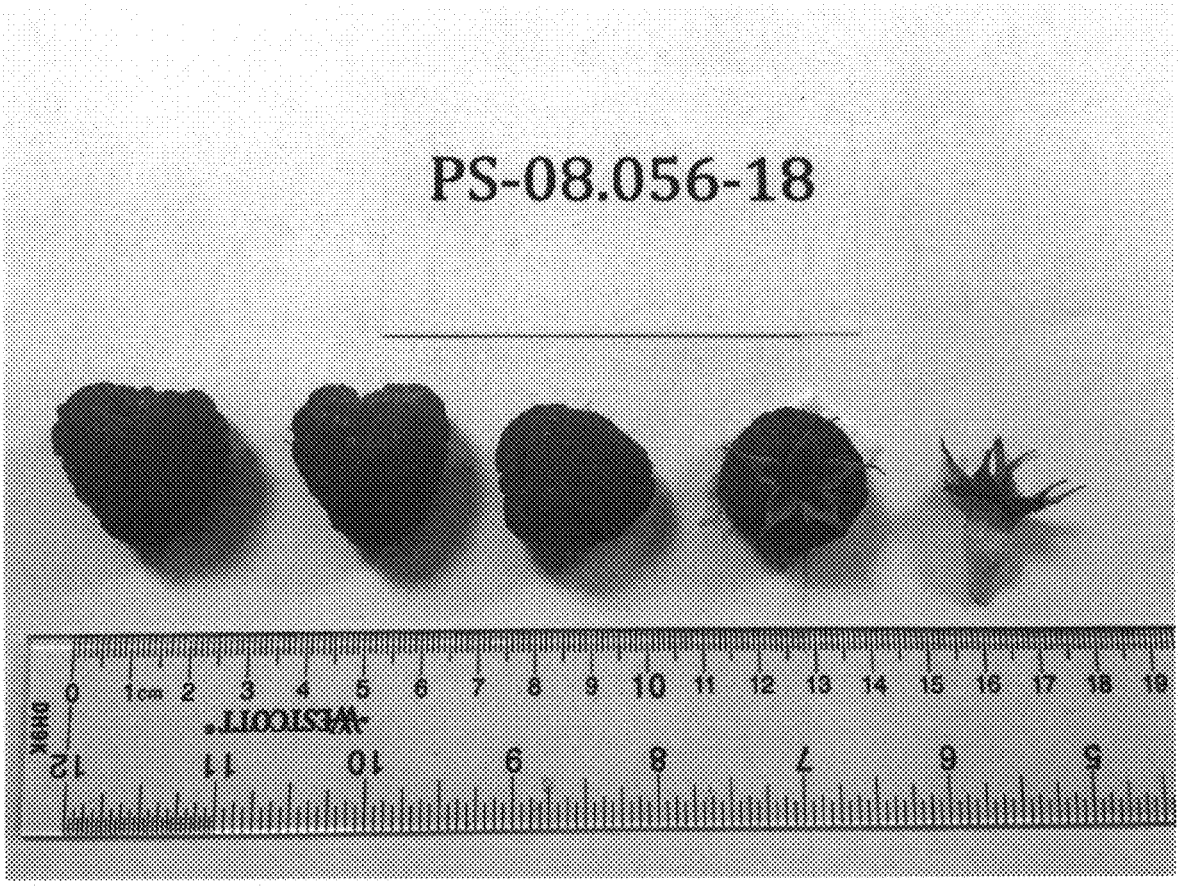
FIG. 3 shows typical gloss, coloration, and drupelet formation of primocane fruit of 'ENDURANCE' taken in the month of September 2020.
Figure 4:
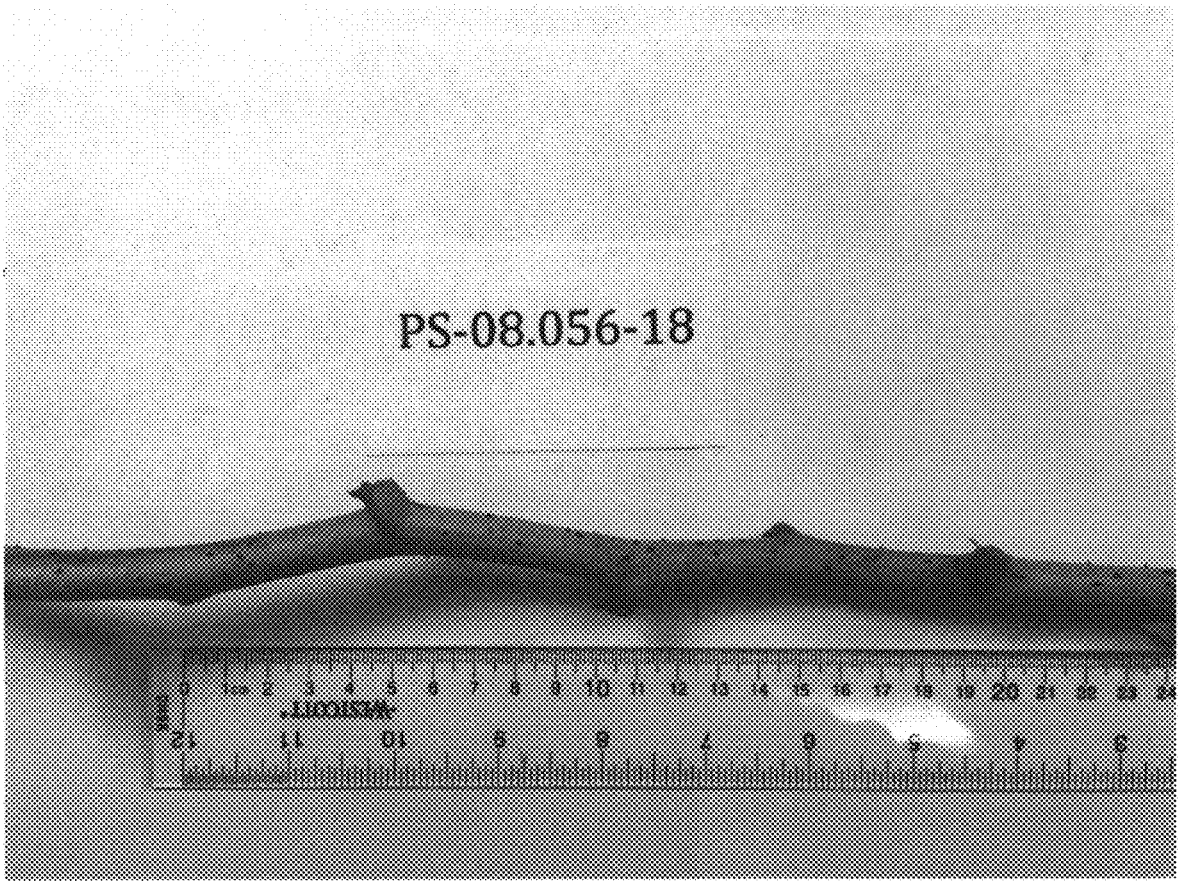
FIG. 4 shows typical primocane and spine coloration of 'ENDURANCE' taken in the month of September 2020.
Figure 5:
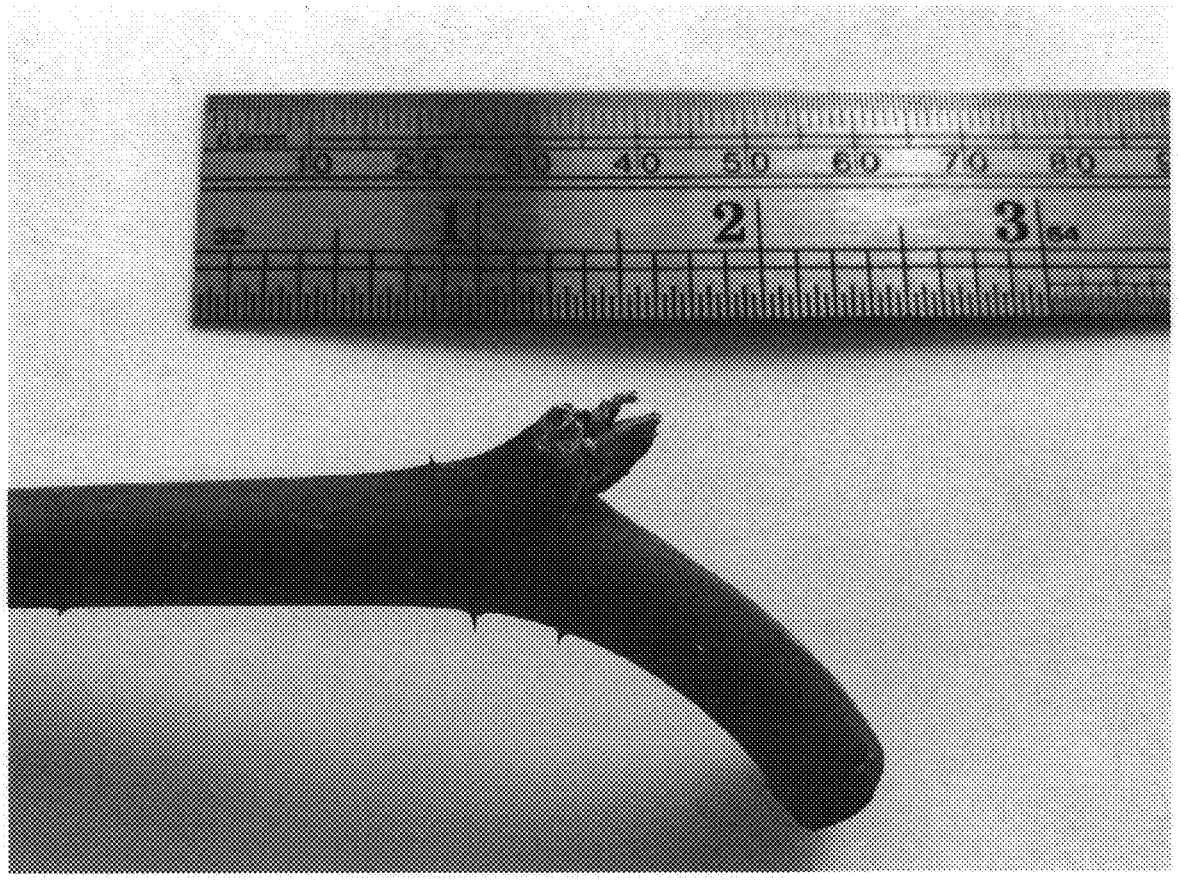
FIG. 5 shows typical dormant bud characteristics of 'ENDURANCE' taken in the month of January 2019.

'ENDURANCE' has not been observed under all possible environmental conditions. The characteristics of the new variety may vary in detail, depending upon variations in environmental factors, including weather (temperature, humidity and light intensity), day length, soil type, and location.

The aforementioned photographs, together with the following description of the new raspberry variety 'ENDURANCE', unless otherwise noted, are based upon observations taken during the 2016-2017 growing season in Watsonville, Calif. Primocane measurements and ratings were taken from plants of 'ENDURANCE' dug from a nursery located in Siskiyou County, Calif. during the middle of October 2015 and planted approximately 3 to 4 weeks later in Watsonville, Calif. The approximate age of the observed primocane plants is 7 to 8 months. Floricane measurements and ratings were taken from the same planting of 'ENDURANCE' at an approximate age of 16 to 18 months. Yield observations and fruit quality characteristics are averaged from 3 years of data collected from the 2015 through 2018 production seasons. Flower measurements and characteristics are from secondary flowers unless otherwise noted. Fruit characteristics and measurements are from secondary fruit unless otherwise noted. Foliage characteristics and measurements are from 3-foliate foliage unless otherwise noted.

Color terminology where noted follows The R.H.S. Colour Chart Fifth Edition, Royal Horticultural Society, London, United Kingdom (2007).

The following tables 3-7 describe fruit, plant, foliage, flower and pest/disease characteristics of the new raspberry 'ENDURANCE' in comparison to the similar raspberry varieties 'GRANDEUR' (patented, U.S. Plant Pat. No. 20,459).

COMPARISON BETWEEN ENDURANCE AND GRANDEUR

TABLE 3

FRUIT CHARACTERISTICS

| Characteristic | 'ENDURANCE' | 'GRANDEUR' (U.S. Plant Pat. No. 20,459) |
|---|---|---|
| Color mature fruit | RHS 42A Medium red | RHS 42A Medium red |
| Color achenes | RHS 159A Orange-white group | RHS 159A Orange-white group |
| Fruit length (mm) | 27.71 | 22.91 |
| Fruit width (mm) | 23.20 | 20.12 |
| Length/Width ratio | 1.19 Longer than broad | 1.14 Longer than broad |
| Seed weight (mg) | 1.76 | 1.75 |
| Drupelets per berry | 95 | 93 |
| Weight of single drupe (g/drupe) | 0.071 | 0.043 |
| Drupe length (mm) | 7.45 | 5.25 |
| Drupe diameter (mm) | 4.53 | 3.86 |
| Relative size of drupes | Large | Medium |
| Fruit size | Medium | Medium |
| Fruit per node | 10 | 15 |
| Predominant shape | Conical | Conical |
| Receptacle length (mm) | 24.74 | 19.15 |
| Receptacle diameter (mm) | 12.02 | 10.32 |
| Receptacle color | RHS 155B White group | RHS 155B White group |
| Evenness of color (fruit) | Even | Even |
| Glossiness | Medium | Medium |
| Adherence of receptacle | Very weak | Very weak |
| Firmness of flesh | Firm | Very firm |
| Firmness of skin | Firm | Very firm |
| Soluble Solids (% brix) | 9.8 | 10.5 |
| Flavor | Fair | Good |
| Shipping quality | Good | Good |
| Fruit storage life (avg) | 9 days | 12 days |
| Fruit market use | Fresh | Fresh |

TABLE 4

PLANT CHARACTERISTICS

| Characteristic | 'ENDURANCE' | 'GRANDEUR' (U.S. Plant Pat. No. 20,459) |
|---|---|---|
| General: | | |
| Habit | Semi-erect | Upright |
| Plant height (m) | 1.5 | 1.4 |
| Plant width (cm) | 38 | 45 |
| Time to initiate roots (days) | 12-14 | 12-14 |
| Canes per hill | 7.5 | 6.9 |
| Productivity | High | High |
| Self-fruitfulness | Yes | Yes |
| Type of bearing | Everbearing | Everbearing |
| Primocane: | | |
| Color (true) | RHS 145A Yellow-green group | RHS 145B Yellow-green group |
| Length (cm) | 153.5 | 143.6 |
| Basal diameter (mm) | 19.26 | 21.80 |

TABLE 4-continued

PLANT CHARACTERISTICS

| Characteristic | 'ENDURANCE' | 'GRANDEUR' (U.S. Plant Pat. No. 20,459) |
|---|---|---|
| Diameter central ⅓ (mm) | 13.76 | 12.55 |
| Lateral length at central ⅓ (cm) | 27.7 | 43.6 |
| No. fruiting laterals per cane | 11.8 | 17.4 |
| Total nodes per cane | 39 | 31 |
| Internode length at central ⅓ (mm) | 38.93 | 48.84 |
| Anthocyanin coloration | RHS 59B Red-purple group | RHS 59B Red-purple group |
| Anthocyanin intensity | Medium | Weak |
| Pubescence | Absent | Absent |
| Vegetative bud length (mm) | 8.70 | 11.01 |
| Vegetative bud diameter (mm) | 5.15 | 6.11 |
| Vegetative bud shape | Widely ovate | Widely ovate |
| Vegetative bud color | RHS 187A Greyed-red group | RHS 187A Greyed-red group |
| Strength of waxy coat (glaucosity) | Absent to very weak | Absent to very weak |
| Time of cane emergence | Medium to late | Medium |
| Time of flowering | Medium to late | Medium |
| Time of fruiting | Medium to late | Medium |
| Length of fruiting season | Long | Long |
| % of total yield | 38% | 50% |
| Flowering period | Late June to Late November | Late June to Late November |
| Harvest period | Late July to Late December | Late July to Late December |
| Primocane fruit weight (g) | 4.7 | 3.8 |
| Primocane yield (g/plant) | 1,936 | 2,662 |
| Young Shoots: | | |
| Number (per meter) | 15-20 Medium | 15-20 Medium |
| Anthocyanin presence | Present | Present |
| Anthocyanin coloration | RHS 179A Red-purple group | RHS 179A Greyed-red group |
| Anthocyanin intensity | Weak | Medium |
| Thorns: | | |
| Thorn presence | Present | Present |
| Thorn coloration (tip) | RHS 187A Greyed-purple group | RHS 180C Greyed-red group |
| Thorn coloration (base) | RHS N186C Greyed-purple group | RHS 145B Yellow-green group |
| Thorn length at central ⅓ (mm) | 1.39 | 0.76 |
| Thorn base at central ⅓ (mm) | 1.32 | 1.53 |
| Thorn density per cm at central ⅓ | 5.25 Medium | 3.38 Medium |
| Thorn texture | Rigid | Rigid |
| Attitude of the tip | Horizontal | Horizontal |
| Floricane: | | |
| Color (true) | RHS 165B Greyed-orange group | RHS 164A Greyed-orange group |
| Length (cm) | 123.4 | 119.8 |
| Width at central ⅓ (mm) | 12.58 | 12.04 |
| Total nodes per cane | 22 | 18 |
| Internode length at central ⅓ (mm) | 44.55 | 49.13 |
| Fruiting lateral attitude | Erect | Erect |
| Time bud burst (vegetative) | Medium | Medium |
| Time of flowering | Medium | Medium |
| Time of fruiting | Medium | Medium |
| Length of fruiting season | Medium to long | Medium to long |
| % of total yield | 62% | 50% |
| Flowering period | Late April to Late June | Late April to Late June |
| Harvest period | Late May to Late July | Late May to Late July |

TABLE 4-continued

| PLANT CHARACTERISTICS | | |
|---|---|---|
| Characteristic | 'ENDURANCE' | 'GRANDEUR' (U.S. Plant Pat. No. 20,459) |
| Floricane fruit weight (g) | 4.6 | 3.7 |
| Floricane yield (g/plant) | 3,161 | 2,680 |

TABLE 5

| FOLIAGE CHARACTERISTICS | | |
|---|---|---|
| Characteristic | 'ENDURANCE' (3 Foliate) | 'GRANDEUR' (U.S. Plant Pat. No. 20,459) (3 Foliate) |
| General: | | |
| Color of upper surface | RHS N137A Green group | RHS N137A Green group |
| Color of lower surface | RHS 190B Greyed-green group | RHS 190B Greyed-green group |
| Venation | Pinnate | Pinnate |
| Shape in cross section | Flat to slightly convex | Flat to slightly convex |
| Arrangement | Compound | Compound |
| Relief between veins (rugosity) | Weak | Strong |
| Glossiness | Weak | Weak |
| Number of leaflets/leaf | Equal 3-5 | Always 3 |
| Total leaf length (cm) | 26.1 | 22.5 |
| Total leaf width (cm) | 24.2 | 23.4 |
| Terminal Leaflet: | | |
| Length (mm) | 165.1 | 127.5 |
| Width (mm) | 120.3 | 91.6 |
| Length/width ratio | 1.4 Longer than broad | 1.4 Longer than broad |
| Size | Large | Medium to large |
| Shape | Lobed | Cordate |
| Shape of base | Cordate | Cordate |
| Shape of tip | Acuminate | Acuminate |
| Margins | Biserrate | Biserrate |
| Lateral Leaflet: | | |
| Length (mm) | 128.3 | 105.5 |
| Width (mm) | 74.1 | 65.1 |
| Length/width ratio | 1.7 Much longer than broad | 1.6 Longer than broad |
| Rachis length (mm) | 41.3 | 36.2 |
| Rachis diameter (mm) | 2.41 | 1.92 |
| Rachis anthocyanin coloration of upper surface | RHS 184B | RHS 184A |
| Rachis anthocyanin intensity | Weak | Medium |
| Orientation | Opposite | Opposite |
| Arrangement | Compound | Compound |
| Relative position of lateral leaflets | Free | Touching |
| Shape | Ovate | Ovate |
| Shape of the base | Rounded | Oblique rounded |
| Shape of the tip | Acuminate | Acuminate |
| Margins | Biserrate | Biserrate |
| Petiole: | | |
| Length (mm) | 54.54 | 59.00 |
| Width (mm) | 3.50 | 3.99 |
| Thorn presence | Yes | Yes |
| Thorn orientation | Erect | Erect |
| Anthocyanin coloration of upper surface | RHS 180B Greyed-purple group | RHS 184C Greyed-purple group |

TABLE 5-continued

| FOLIAGE CHARACTERISTICS | | |
|---|---|---|
| Characteristic | 'ENDURANCE' (3 Foliate) | 'GRANDEUR' (U.S. Plant Pat. No. 20,459) (3 Foliate) |
| Anthocyanin intensity of upper surface | Absent to very weak | Weak |
| Stipule length (mm) | 12.77 | 10.23 |
| Stipule orientation | Erect | Erect to horizontal |

TABLE 6

| FLOWER CHARACTERISTICS | | |
|---|---|---|
| Characteristic | 'ENDURANCE' | 'GRANDEUR' (U.S. Plant Pat. No. 20,459) |
| Petal color (upper surface) | RHS 155C White group | RHS 155C White group |
| Petal color (lower surface) | RHS 155C White group | RHS 155C White group |
| Flower diameter (mm) | 27.25 | 22.55 |
| Petal length (mm) | 8.25 | 6.42 |
| Petal width (mm) | 3.42 | 3.11 |
| Petal length/width ratio | 2.41 Much longer than broad | 2.06 Much longer than broad |
| Petal shape in cross section | Flat | Flat |
| Petal shape (overall) | Ovate | Ovate |
| Petal shape (apex) | Rounded | Rounded |
| Petal shape (base) | Attenuate | Attenuate |
| Petal margin | Entire | Entire |
| Petal texture | Glabrous | Glabrous |
| No. petals/flower | 5.2 | 5.2 |
| No. sepals/flower | 5.2 | 5.2 |
| Sepal length (mm) | 10.80 | 11.20 |
| Sepal width at base (mm) | 4.41 | 6.49 |
| Sepal shape | Deltate | Widely deltate |
| Sepal shape (apex) | Acuminate | Acuminate |
| Sepal coloration (upper surface) | RHS 144A | RHS 144B |
| Sepal coloration (lower surface) | RHS 144B | RHS 144C |
| Sepal margin | Entire | Entire |
| Sepal texture | Slightly pubescent | Slightly pubescent |
| No. stamen/flower | 116 | 105 |
| Filament length (mm) | 5.19 | 4.45 |
| Filament color | RHS 155C White group | RHS 155C White group |
| Pollen quantity | Medium | Medium |
| Pollen color | RHS 196D | RHS 196D |
| Anther length (mm) | 1.16 | 0.79 |
| Anther diameter (mm) | 0.53 | 0.49 |
| Anther coloration (pre-dehiscence) | RHS 155C | RHS 155C |
| Anther coloration (post-dehiscence) | RHS 165B | RHS 165B |
| Stigma shape | Lobed | Lobed |
| Stigma length (mm) | 0.12 | 0.10 |
| Stigma diameter (mm) | 0.42 | 0.40 |
| Stigma coloration | RHS 145D | RHS 145D |
| Style length (mm) | 3.08 | 2.03 |
| Style diameter (mm) | 0.40 | 0.39 |
| Style coloration | RHS 145D | RHS 145D |
| Ovule length (mm) | 1.56 | 1.51 |
| Ovule diameter (mm) | 1.47 | 1.40 |
| Ovule coloration | RHS 145B | RHS 145B |
| Pedicle length (mm) | 21.55 | 23.86 |
| Pedicle diameter (mm) | 1.51 | 1.47 |
| Pedicle anthocyanin coloration | RHS 181C | RHS 178A |
| Pedicle anthocyanin intensity | Absent to very weak | Medium |

TABLE 6-continued

| FLOWER CHARACTERISTICS | | |
|---|---|---|
| Characteristic | 'ENDURANCE' | 'GRANDEUR' (U.S. Plant Pat. No. 20,459) |
| Relative number of pedicel | 26.9 | 16.2 |
| thorns | Many | Medium |
| Peduncle anthocyanin presence | Present | Present |
| Peduncle anthocyanin coloration | RHS 184C Greyed-purple group | RHS 184A Greyed-purple group |
| Peduncle anthocyanin intensity | Weak | Medium |

TABLE 7

| PEST AND DISEASE REACTIONS | | |
|---|---|---|
| Characteristic | 'ENDURANCE' | 'GRANDEUR' (U.S. Plant Pat. No. 20,459) |
| Spotted wing drosophila (Drosophila suzukii) | Susceptible | Susceptible |
| Two spotted spider mite (Tetranychus urticae) | Susceptible | Susceptible |
| Grey fruit mold (Botrytis cinerea) | Susceptible | Susceptible |
| Powdery mildew (Podosphaera aphanis var. aphanis) | Moderately resistant | Moderately susceptible |
| Yellow rust (Phragmidium rubi-idaei) | Moderately resistant | Moderately susceptible |

I claim:

1. A new and distinct raspberry plant named 'ENDURANCE', as described and illustrated herein.

* * * * *